United States Patent [19]

Bunnell et al.

[11] Patent Number: 5,736,541
[45] Date of Patent: Apr. 7, 1998

[54] OLANZAPINE POLYMORPH CRYSTAL FORM

[75] Inventors: Charles Arthur Bunnell, Lafayette, Ind.; Barry Arnold Hendriksen, Guildford, United Kingdom; Samuel Dean Larsen, West Lafayette, Ind.

[73] Assignees: Eli Lilly and Company, Indianapolis, Ind.; Eli Lilly and Company, Basingstoke, England

[21] Appl. No.: 686,989

[22] Filed: Jul. 25, 1996

Related U.S. Application Data

[63] Continuation-in-part of Ser. No. 409,566, Mar. 24, 1995, abandoned.

[51] Int. Cl.[6] .......................... A01N 43/62; C07D 243/10
[52] U.S. Cl. .............................. 514/220; 540/557
[58] Field of Search ........................... 540/557; 514/220

[56] References Cited

U.S. PATENT DOCUMENTS

| | | | |
|---|---|---|---|
| 4,115,568 | 9/1978 | Chakrabarti et al. | 424/250 |
| 4,115,574 | 9/1978 | Chakrabarti et al. | 540/557 |
| 5,229,382 | 7/1993 | Chakrabarti et al. | 514/220 |
| 5,457,101 | 10/1995 | Greenwood et al. | 514/220 |

FOREIGN PATENT DOCUMENTS

| | | |
|---|---|---|
| 0 582 368 | 9/1994 | European Pat. Off. . |
| 733635 | 9/1997 | European Pat. Off. . |

OTHER PUBLICATIONS

J. K. Chakrabarti, et al., *J. Med. Chem.*, 23, pp. 878–884, (1980).

*Primary Examiner*—Mukund J. Shah
*Assistant Examiner*—Tamthom T. Ngo
*Attorney, Agent, or Firm*—MaCharri Vorndran-Jones; David E. Boone

[57] ABSTRACT

The invention provides Form II, a pharmaceutically elegant, stable polymorph of olanzapine useful for treating a condition selected from the group consisting of a psychotic condition, mild anxiety and gastrointestinal conditions.

25 Claims, No Drawings

OLANZAPINE POLYMORPH CRYSTAL FORM

This application is a continuation-in-part of U.S. Ser. No. 08/409,566, filed Mar. 24 1995, now abandoned.

FIELD OF THE INVENTION

This invention relates to a novel form of 2-methyl-4-(4-methyl-1-piperazinyl)-10H-thieno[2,3-b][1,5]benzodiazepine (hereinafter referred to by its generic name "olanzapine"), more specifically to a novel crystalline form of that compound and to pharmaceutical formulations containing that novel form as an active ingredient.

BACKGROUND OF THE INVENTION

A novel crystal form of olanzapine has now been synthesized and characterized which possesses distinct advantages over the previously known form, that is the material produced using the methods described in U.S. Pat. No. 5,229,382 (hereinafter referred to as "the '382 patent"), and which is clearly distinguishable therefrom by x-ray powder diffractometry. The first form of olanzapine (hereinafter referred to as "Form I"), as prepared by the procedures described in the '382 patent, has been found to be metastable and not well suited for commercial use in pharmaceutical formulations. However, in accordance with the present invention, a newly discovered second polymorph of olanzapine, which will be designated hereinafter as "Form II", has been found to be obtainable in highly pure form, that is free from Form I and contamination by solvates such as water or acetonitrile, is stable, pharmaceutically elegant, and therefore well adapted for commercial use in pharmaceutical formulations such as tablets.

Olanzapine has shown great promise in the treatment of psychotic patients and is currently being evaluated for that purpose. Unfortunately, olanzapine prepared using the methods described in the '382 patent typically exhibits a color which is undesirable for commercial pharmaceutical use, especially since the color was found to change over time on exposure to air. Even carbon treatment of the olanzapine prepared using the methods described in the '382 patent does not remove all of the undesired color. Such a pharmaceutical which changes color over time could be particularly troublesome for psychotic patients if a dosage form, such as a tablet, were to be chosen where color changes were apparent. Therefore, greater purity and freedom from color change are desirable. The novel polymorph of this invention provides precisely the longed for pharmaceutically elegant and desirable properties needed for a drug to be administered to psychotic patients, and has satisfactory color stability and is substantially free of undesired solvating agents such as water and acetonitrile.

SUMMARY OF THE INVENTION

The present invention provides Form II olanzapine polymorph having a typical x-ray powder diffraction pattern as represented by the following interplanar spacings:

| d |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007 |

A typical example of an x-ray diffraction pattern for Form II is as follows wherein d represents the interplanar spacing and $I/I_1$ represents the typical relative intensities:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

The x-ray diffraction patterns set out herein were obtained using a Siemens D5000 x-ray powder diffractometer having a copper $K_\alpha$ radiation source of wavelength, $\lambda=1.541$ Å.

The invention further provides the Form II polymorph in substantially pure form.

The present invention also provides a pharmaceutical formulation, such as a tablet, comprising Form II as an active ingredient, associated with one or more pharmaceutical acceptable excipients. In another embodiment of the invention, there is provided a method for using Form II for treating a psychotic condition, mild anxiety, gastrointestinal conditions and for providing pharmaceutical formulations for use in such methods.

DETAILED DESCRIPTION OF THE INVENTION

The polymorph obtainable by the process taught in the '382 patent will be designated as Form I and has a typical x-ray powder diffraction pattern substantially as follows, wherein d represents the interplanar spacing:

| d |
|---|
| 9.9463 |
| 8.5579 |
| 8.2445 |
| 6.8862 |
| 6.3787 |
| 6.2439 |
| 5.5895 |
| 5.3055 |
| 4.9815 |
| 4.8333 |
| 4.7255 |
| 4.6286 |
| 4.533 |
| 4.4624 |
| 4.2915 |
| 4.2346 |
| 4.0855 |
| 3.8254 |
| 3.7489 |
| 3.6983 |
| 3.5817 |
| 3.5064 |
| 3.3392 |
| 3.2806 |
| 3.2138 |
| 3.1118 |
| 3.0507 |
| 2.948 |
| 2.8172 |
| 2.7589 |
| 2.6597 |
| 2.6336 |
| 2.5956 |

A typical example of an x-ray diffraction pattern for Form I is as follows wherein d represents the interplanar spacing and $I/I_1$ represents the typical relative intensities:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |

-continued

| d | $I/I_1$ |
|---|---|
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper $K_\alpha$ of wavelength $\lambda=1.541$ Å. The patterns were obtained using a Siemens D5000 x-ray powder diffractometer. The interplanar spacings in the column marked "d" are in Angstroms. The typical relative intensities are in the column marked "$I/I_1$".

The novel form of olanzapine provided by this invention is rather difficult to prepare in substantially pure form. However, in accordance with the invention, it has been discovered that when olanzapine of reasonably high purity, that is of technical grade (that is olanzapine containing less than about 5% undesired related substances and preferably less than about 1% undesired related substances and see Example 1), is dissolved in ethyl acetate under anhydrous conditions, Form II can be crystallized out of the solution so formed in substantially pure form, that is free from the undesired polymorph or solvates such as water or acetonitrile. Anhydrous conditions refer to less than one percent water present in the ethyl acetate.

In preparing Form II according to the invention, the technical grade olanzapine can be dissolved in the ethyl acetate by agitation such as stirring and the like. Crystallization from the resulting solution can be by any conventional process including seeding, chilling, scratching the glass of the reaction vessel, and other such common techniques.

As used herein "substantially pure" refers to Form II associated with less than about 5% Form I, preferably less than about 2% Form I, and more preferably less than about 1% Form I. Further, "substantially pure" Form II will contain less than about 0.5% related substances, wherein "related substances" refers to undesired chemical impurities or residual solvent or water. In particular, "substantially pure" Form II should contain less than about 0.05% content of acetonitrile, more preferably, less than about 0.005% content of acetonitrile. Additionally, the polymorph of the invention should contain less than 0.5% of associated water.

Advantageously, the novel polymorph of the invention will be free from solvates, for instance existing as the anhydrate.

Pharmaceutical formulations containing Form II should contain less than about 10% Form I, more preferably less than about 5% Form I polymorph.

Olanzapine has useful central nervous system activity. This activity has been demonstrated using well-established procedures, for example, as described in the '382 patent. Form II provided by the present invention appears to have the same profile of receptor activity and has the same therapeutic uses as olanzapine described in the '382 patent.

Therefore, Form II is useful for the treatment of schizophrenia, schizophreniform disorders, psychosis, mild anxiety states, and functional bowel disorders.

As used herein the term "psychotic condition" shall refer to pathologic psychological conditions which are psychoses or may be associated with psychotic features. Such conditions include, but are not limited to the following disorders which have been characterized in the DSM-III-R. *Diagnostic and Statistical Manual of Mental Disorders, Revised*, 3rd Ed. (1980). The DSM-III-R was prepared by the Task Force on Nomenclature and Statistics of the American Psychiatric Association, and provides clear descriptions of diagnostic categories. The numbers in parenthesis refer to the DSM-III-R categories. The skilled artisan will recognize that there are alternative nomenclatures, nosologies, and classification systems for pathologic psychological conditions and that these systems evolve with medical scientific progress.

Examples of pathologic psychologic conditions which may be treated using Form II include, but are not limited to, Conduct Disorder, Group Type (312.20), Conduct Disorder, Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Multi-infarct dementia, with Delirium (290.41), Multi-infarct dementia, with Delusions (290.42), Multi-infarct dementia, with Depression (290.43), Multi-infarct dementia, Uncomplicated (290.40), Senile Dementia NOS (290.00), Presenile Dementia NOS (290.10), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delirium (292.81), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP) or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Mood Disorder (292.84), Phencyclidine (PCP) or Similarly Acting Arylcyclohexylamine Organic Mental Disorder NOS (292.90), Other or Unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.82), Organic Mood Disorder (293.83), Organic Anxiety Disorder (294.80), Organic Mental Disorder (294.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and impulse Control Disorder NOS (312.39).

Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Subchronic (295.11), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic (295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, Unspecified (295.60), Delusional (Paranoid) Disorder (297.10), Brief Reactive Psychosis (298.80), Schizophreniform Disorder (295.40), Schizoaffective Disorder (295.70), induced Psychotic Disorder (297.30), Psychotic Disorder NOS (Atypical Psychosis) (298.90), Bipolar Disorder, Mixed, Severe, without Psychotic Features (296.63), Bipolar Disorder, Manic, Severe, without Psychotic Features (296.43), Bipolar Disorder, Depressed, Severe, without Psychotic Features (296.53), Major Depression, Single Episode, Severe, without Psychotic Features (296.23), Major Depression, Recurrent, Severe, without Psychotic Features (296.33), Bipolar Disorder, Mixed, with Psychotic Features (296.64), Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), and Major Depression, Recurrent with Psychotic Features (296.34).

Preferably, an effective amount of Form II is used for the treatment of Tourette's Disorder; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified;

Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, with Psychotic Features; Hebephrenic Schizophrenia; Post-Schizophrenic Depression; Delusional Disorder; and Other Persistent Delusional Disorders.

More preferredly, Form II is used to treat the following pathologic psychological conditions including Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, with Psychotic Features; Hebephrenic Schizophrenia; Post-Schizophrenic Depression; Delusional Disorder; and Other Persistent Delusional Disorders.

Examples of conditions which are most preferredly treated using Form II include Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; and Hebephrenic Schizophrenia.

Examples of anxiety disorders which may more preferredly be treated using an effective amount of Form II include Psychoactive Substance Anxiety Disorder; Organic Anxiety Disorder; Obsessive Compulsive Disorder; Post-traumatic Stress Disorder; Generalized Anxiety Disorder; and Anxiety Disorder NOS.

Examples of the anxiety disorders which are most preferredly treated using Form II include Organic Anxiety Disorder; Obsessive Compulsive Disorder; Post-traumatic Stress Disorder; Generalized Anxiety Disorder; and Anxiety Disorder NOS.

As used herein the term "Functional Bowel Disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "Functional Bowel Disorder" includes but is not limited to irritable bowel syndrome, hypermotility, ichlasia, hypertonic lower esophogeal sphinctor, tachygastria, constipation, hypermotility associated with irritable bowel syndrome.

Functional Bowel Disorders are characterized by abnormal bowel function without detectable structural abnormalities. Abnormal bowel function includes diarrhea, constipation, mucorrhea, and pain or discomfort over the course of the sigmoid colon. Such disorders are influenced by psychological factors and stressful life situations.

Form II is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient, although divided doses may be administered. For treatment of central nervous system disorders, a dose range of from 1 to 30 mg, preferably 2.5 to 20 mg per day is suitable.

Form II will normally be administered orally and, for this purpose, it is usually employed in the form of a pharmaceutical formulation.

Accordingly, pharmaceutical formulations comprising Form II as active ingredient, associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient. For example, one such preferred quick release formulation is described in U.S. Pat. Nos. 5,079,018, 5,039,540, 4,305,502, 4,758,598, and 4,371,516, hereby incorporated by reference.

Depending on the method of administration, the compositions for the treatment of central nervous system conditions may be formulated as tablets, capsules, gel or suspension for transdermal delivery; suspensions or elixirs for oral use or suppositories. Preferably the compositions are formulated in a unit dosage form, each dosage containing from 0.25 to 100 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 75 mg or 1 to 30 mg of active ingredient together with a pharmaceutically acceptable carrier therefor.

The starting materials for the present invention can be prepared by a variety of procedures well known to those of ordinary skill in the art. The material to be employed as starting materials in the process of this invention can be prepared by the general procedure taught by Chakrabarti in U.S. Pat. No. 5,229,382 ('382), herein incorporated by reference in its entirety.

The following examples are provided for purposes of illustration and are not to be construed as limiting the scope of the claimed invention.

Compound characterization methods include, for example, x-ray powder pattern analysis, thermogravimetric analysis (TGA), differential scanning calorimetery (DSC), titrametric analysis for water, and $H^1$-NMR analysis for solvent content.

EXAMPLE 1

Technical Grade olanzapine

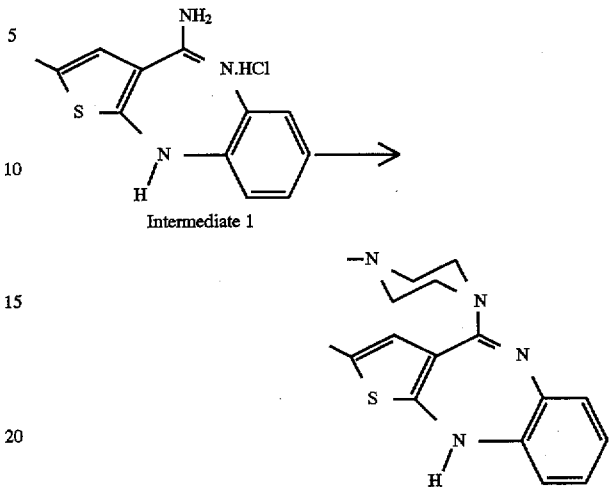

In a suitable three neck flask the following was added:
Dimethylsulfoxide (analytical): 6 volumes
Intermediate 1 : 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained at that temperature throughout the duration of the reaction. The reactions were followed by HPLC until ≦5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

EXAMPLE 2

Form II

A 270 g sample of technical grade 2-methyl-4-(4-methyl-1-piperazinyl)-10H-thieno[2,3-b][1,5]benzodiazepine was suspended in anhydrous ethyl acetate (2.7 L) The mixture was heated to 76° C. and maintained at 76° C. for 30 minutes. The mixture was allowed to cool to 25° C. The resulting product was isolated using vacuum filtration. The product was identified as Form II using x-ray powder analysis.

Yield: 197 g.

The process described above for preparing Form II provides a pharmaceutically elegant product having potency ≧97%, total related substances <0.5% and an isolated yield of >73%.

EXAMPLE 3

Tablet Formulation

A tablet formulation was made by granulating the active with appropriate diluent, lubricant, disintegrant and binder and compressing

| | |
|---|---|
| Form II olanzapine | 10.0 mg |
| Magnesium stearate | 0.9 mg |
| Microcrystalline cellulose | 75.0 mg |
| Povidone | 15.0 mg |
| Starch, directly compressible | 204.1 mg |

EXAMPLE 4

Tablet Formulation

A portion of hydroxypropyl cellulose was dissolved in purified water to form a solution for granulation. The remaining hydroxypropyl cellulose (total of 4.0% w/w final tablet weight), which was an extra fine grade, was combined with the Form II (1.18% w/w), lactose (79.32% w/w) and a portion of crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The outside powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (1.5% w/w) was mixed with purified water to form a solution. Core tablets were divided into approximately equal sections and spray coated with the hydroxypropyl methylcellulose solution The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

What is claimed is:

1. Form II olanzapine polymorph having a typical x-ray powder diffraction pattern as represented by the following interplanar spacings:

| d (Å) |
|---|
| 10.2689 |
| 8.577 |
| 7.4721 |
| 7.125 |
| 6.1459 |
| 6.071 |
| 5.4849 |
| 5.2181 |
| 5.1251 |
| 4.9874 |
| 4.7665 |
| 4.7158 |

-continued

| d (Å) |
|---|
| 4.4787 |
| 4.3307 |
| 4.2294 |
| 4.141 |
| 3.9873 |
| 3.7206 |
| 3.5645 |
| 3.5366 |
| 3.3828 |
| 3.2516 |
| 3.134 |
| 3.0848 |
| 3.0638 |
| 3.0111 |
| 2.8739 |
| 2.8102 |
| 2.7217 |
| 2.6432 |
| 2.6007. |

2. Form II as claimed in claim 1 which is substantially pure.

3. Form II as claimed in claim 2 which contains less than about 5% Form I as hereinbefore defined.

4. Form II as claimed in claim 3 which contains less than about 2% content of Form I as hereinbefore defined.

5. Form II as claimed in claim 1 which is solvate free.

6. Form II as claimed in claim 2 which is anhydrous.

7. A pharmaceutical formulation comprising as an active ingredient Form II as claimed in claim 1 associated with one or more pharmaceutically acceptable carriers, excipients, or diluents therefor.

8. A pharmaceutical formulation as claimed in claim 7 which is a tablet.

9. A pharmaceutical formulation of claim 7 wherein the formulation is solvate free.

10. A process for preparing Form II olanzapine polymorph comprising slurrying technical grade olanzapine in ethyl acetate under anhydrous conditions and crystallizing Form II from the solution so formed.

11. A method for treating a condition selected from the group consisting of a psychotic condition, mild anxiety and gastrointestinal conditions comprising administering an effective amount of Form II as claimed in claim 1 to a patient in need thereof.

12. A method of claim 11 wherein the condition is schizophrenia or a schizophreniform disorder.

13. A pharmaceutical formulation comprising as an active ingredient Form II as claimed in claim 2 associated with one or more pharmaceutically acceptable carriers, excipients, or diluents therefor.

14. A Form II olanzapine polymorph as claimed by claim 2 which contains less than about ten percent (10%) Form I olanzapine polymorph.

15. A Form II olanzapine polymorph as claimed by claim 2 which contains less than one half percent (0.5%) related substances.

16. A Form II olanzapine polymorph as claimed in claim 1 further characterized by substantially the following x-ray powder diffraction pattern wherein d represents the interplanar spacing and $I/I_1$ represents the typical relative intensities:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77. |

17. A Form II olanzapine polymorph as claimed by claim 16 which is substantially pure.

18. A Form II olanzapine polymorph as claimed by claim 17 which contains less than about 5% Form I olanzapine polymorph.

19. A Form II olanzapine polymorph as claimed by claim 16 which is solvate free.

20. A Form II olanzapine polymorph as claimed by claim 17 which is anhydrous.

21. A pharmaceutical formulation comprising as an active ingredient Form II olanzapine polymorph as claimed by claim 16 associated with one or more pharmaceutically acceptable carriers, excipients, or diluents therefor.

22. A method for treating a condition selected from the group consisting of a psychotic condition, mild anxiety and gastrointestinal conditions comprising administering an effective amount Form II olanzapine polymorph as claimed in claim 16 to a patient in need thereof.

23. A pharmaceutical formulation comprising as an active ingredient Form II olanzapine polymorph as claimed in claim 17 associated with one or more pharmaceutically acceptable carriers, excipients, or diluents therefor.

24. A Form II olanzapine polymorph as claimed by claim 17 which contains less than about ten percent (10%) Form I olanzapine polymorph.

25. A Form II olanzapine polymorph as claimed by claim 17 which contains less than one half percent (0.5%) related substances.

* * * * *